US010046257B2

(12) United States Patent
Bosio et al.

(10) Patent No.: US 10,046,257 B2
(45) Date of Patent: Aug. 14, 2018

(54) STACKABLE CELL STRAINER

(71) Applicant: Miltenyi Biotec GmbH, Bergisch Gladbach (DE)

(72) Inventors: Andreas Bosio, Bergisch Gladbach (DE); Eiad Kabaha, Bergisch Gladbach (DE); Carsten Poggel, Bergisch Gladbach (DE); Timo Adams, Bergisch Gladbach (DE); Wolfgang Stoters, Bergisch Gladbach (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 364 days.

(21) Appl. No.: 13/875,124

(22) Filed: May 1, 2013

(65) Prior Publication Data
US 2013/0306576 A1 Nov. 21, 2013

(30) Foreign Application Priority Data

May 15, 2012 (EP) .................... 12167980

(51) Int. Cl.
*B01D 24/38* (2006.01)
*B01D 29/88* (2006.01)
(Continued)

(52) U.S. Cl.
CPC .......... *B01D 35/306* (2013.01); *B01L 3/5021* (2013.01); *C12M 47/02* (2013.01);
(Continued)

(58) Field of Classification Search
CPC .. A47J 31/02; A47J 31/06; A47J 43/20; A47J 43/22; A47J 43/24; A61M 1/0209;
(Continued)

(56) References Cited

U.S. PATENT DOCUMENTS 2,136,170 A 11/1938 Luertzing
2,331,234 A 10/1943 Rush
(Continued)

FOREIGN PATENT DOCUMENTS

CH 241194 A 2/1946
CN 102120111 A 7/2011
(Continued)

OTHER PUBLICATIONS

European Search Report and European Search Opinion dated Oct. 1, 2012, for European Patent Application No. 12167980.7, filed on May 15, 2012, six pages.

*Primary Examiner* — Hayden Brewster
(74) *Attorney, Agent, or Firm* — Morrison & Foerster LLP

(57) ABSTRACT

A cell strainer for separating particles from a cell suspension, having an upper portion with at least one filter area lying essentially perpendicular to the direction of flow of the suspension and a lower portion adapted to fit into the openings of at least two sample tubes with different sized openings. The lower portion has a first section with shoulders or flanges having the diameter of the opening of a first tube and a second section having an inner and outer wall serving as a receptacle for the neck of a second tube, where the diameter of the first section is larger than the diameter of the second section.

12 Claims, 5 Drawing Sheets

(51) Int. Cl.

| | |
|---|---|
| *B01D 35/02* | (2006.01) |
| *B01D 35/30* | (2006.01) |
| *B01L 3/00* | (2006.01) |
| *C12M 1/00* | (2006.01) |
| *B01L 3/02* | (2006.01) |
| *B01D 35/00* | (2006.01) |
| *B01D 41/00* | (2006.01) |

(52) U.S. Cl.
CPC . *B01L 2200/023* (2013.01); *B01L 2200/0684* (2013.01); *B01L 2300/0681* (2013.01); *B01L 2300/087* (2013.01)

(58) Field of Classification Search
CPC ........ A61M 1/3633; A61M 2202/0439; B01D 29/085; B01D 23/28; B01D 24/00; B01D 24/38; B01D 24/105; B01D 25/00; B01D 27/00; B01D 29/00; B01D 29/88; B01D 33/00; B01D 33/35; B01D 35/00; B01D 35/02; B01D 35/12; B01D 35/16; B01D 35/22; B07B 1/06; B65B 39/00; B65B 2039/008; B67C 11/00; B67C 11/02; B67C 11/04; B67C 2011/20
USPC ................. 141/331–343; 210/232, 359, 464, 210/469–474, 477, 481, 482, 484, 497.01, 210/497.2, 497.3, 499, 767, 808
See application file for complete search history.

(56) References Cited

U.S. PATENT DOCUMENTS

| | | | |
|---|---|---|---|
| 2,703,670 A | | 3/1955 | Voight |
| 4,689,147 A | * | 8/1987 | Leoncavallo .......... B01D 29/05 210/232 |
| 4,702,834 A | * | 10/1987 | Relyea ................. B01D 29/012 210/321.78 |
| 5,071,549 A | | 12/1991 | Häuslein |
| 5,762,120 A | | 6/1998 | Smith |
| 6,035,907 A | * | 3/2000 | DeCoster ...................... 141/331 |
| 6,425,424 B1 | * | 7/2002 | Ellis Calvo ............. B65B 39/00 141/331 |
| 2003/0080045 A1 | * | 5/2003 | Zuk, Jr. .................. B01D 29/05 210/416.1 |
| 2011/0171085 A1 | | 7/2011 | Bucher |
| 2012/0152865 A1 | * | 6/2012 | Lin ................................ 210/808 |
| 2012/0315633 A1 | * | 12/2012 | Mantzaris et al. ........... 435/6.11 |
| 2013/0199667 A1 | * | 8/2013 | Kent ....................... B67C 11/02 141/331 |

FOREIGN PATENT DOCUMENTS

| | | |
|---|---|---|
| EP | 0 593 767 B1 | 4/1994 |
| EP | 1 843 852 B1 | 10/2007 |
| GB | 371618 | 4/1932 |
| JP | 2001-510999 A | 8/2001 |
| WO | WO-98/32875 A1 | 7/1998 |
| WO | WO-2009/096790 A1 | 8/2009 |

* cited by examiner

STACKABLE CELL STRAINER

CROSS REFERENCE TO RELATED APPLICATIONS

This application claims priority to European Application No. 12167980.7 filed May 15, 2012, incorporated herein by reference in its entirety.

FIELD OF THE INVENTION

This invention relates to a filter system for removing particles above a certain diameter from a suspension containing single cells or cellular compartments using the filter system with laboratory vessels.

BACKGROUND

In biological research or diagnosis in medicine, it is often required to dissociate a sample, such as tissue, into isolated cells. Tissue dissociation is often achieved by enzymatic digestions and/or mechanical dissection using fragmentation devices, for example as disclosed in European Patent EP1843852 B1. In the case of dissociation, the single-cells are separated from dissociated tissue fragments by filtration.

Filter systems for biological research or diagnosis in medicine are long known. Gauze was initially used for separating isolated cells from bigger particles or tissue. As gauze absorbs the liquid of the sample in part, so called cell strainers having a mesh for filtration are used for this purpose. Cells strainers are available in several mesh sizes depending on the particles to be separated, for example on the size of the target cells.

Since the most common laboratory vessels for biological research or in medical diagnosis (testing) are so called tubes (also called "test tubes"), i.e. small cylindrical-shaped vessels with a flip or screw cap, it is desired to perform the filtration into such tubes without the need for further handling of the sample. Such tubes are available for several different volumes, thereby having different sized openings. For researchers working with cells, especially 15 ml and 50 ml volume are common tube formats.

Commercially available cell strainers for laboratory use are disposable, sterile packed and available for use with different vessels and applications. For example, European Patent EP 0593767, Swiss Patent CH241194 or U.S. Pat. No. 2,331,234 disclose filter systems which are inserted into a vessel such as a tube so that the filter flange is supported by the opening of the vessel. In other words, the filter systems hangs inside the tube, which means that this filter system only works with the tube size it is designed for.

A similar filter system is disclosed in International Patent Publication WO 2009/096790 A1, where the filter is provided with a plurality of supporting edges which fit to the outside of a vessel. The filter rests via the supporting edges on the vessel. Filters in the prior art simply sitting on top of a vessel (tube) tend to tilt over.

Filters in the prior art hanging inside a vessel (tube) leave essentially no space between the side walls of the filter and the vessel, which impairs venting when the filter is filled with liquid (e.g., a suspension). The result is a "flow stop", especially if a slightly viscous sample is processed, and then the filter needs to be lifted up manually to clear it. The filter area is provided in a frame with a grip handle in order to handle the filter and preserve aseptic conditions without touching the filter's sieve area. However, the grip handle is quite small and difficult to handle under the usual working conditions in a laboratory. Furthermore, the volume of the filter system above the sieve is too small to hold the sample volume of a standard tube, which makes refilling necessary if liquid does not run through the sieve immediately during pipetting.

Furthermore, filter systems designed for laboratory vessels having a small volume are usually of small size with a small filter area. Small filter areas tend to clog and/or their processing speed is rather low. On the other hand, use of tubes with a smaller diameter has clear advantages in reduced wash volumes, rack space, higher number of samples to be processed with a centrifuge and better pellet formation after centrifugation.

Accordingly there is a need for a filter system which provides sufficient filter efficiency but is also compatible with small tube sizes.

SUMMARY OF THE INVENTION

A goal of the invention is to provide a cell strainer which has high filter efficiency and is compatible with tubes of different opening sizes, i.e. fits on at least both the standard 15 ml and 50 ml laboratory tubes.

This goal is accomplished with a cell strainer for separating particles from a cell suspension, having an upper portion with at least one filter area lying essentially perpendicular to the direction of flow of the suspension and a lower portion adapted to fit into the openings of at least two tubes with different sized openings, where the lower portion has a first section having shoulders or flanges which have the diameter of the opening of a first tube and a second section having an inner and outer wall as a receptacle for the neck of a second tube, where the diameter of the first section is larger than the diameter of the second section.

The inner and outer walls of the second section are formed to accommodate the neck of a second tube, i.e. are shaped as a receptacle in order to fit to the second tube. The receptacle should fit to the second tube to provide a force-fitting hold to the tube, to prevent the cell strainer from tilting from the tube. The inner and outer wall of the second section of the cell strainer according to the invention enable tilt-free stacking of the cell strainer on at least two different standard tubes (e.g., 15 ml and 50 ml tubes). In addition, the cell strainer can be easily removed from the tubes since the cell strainer is stacked on the tube and not clipped or screwed on.

The filter area which is lying essentially perpendicular to the direction of flow of the suspension may lie in a plane exactly perpendicular to the direction of flow or slightly deviated (e.g., at an angle of 0° to 15°) from the perpendicular to the direction of flow.

The cell strainer according to the invention can be used for separating particles from a cell suspension. Separating particles includes, for example, separating single cells from tissue which has been dissociated mechanically (such as grinding or fragmenting) or chemically (such as enzymatic digestion). In this case, target cells are separated from unwanted particles. Furthermore, separating particles includes the separation of cellular compartments such as mitochondria, nuclei, ribosomes and vesicles obtained by disintegrating cells from intact cells or tissue. Also the cell strainer can be used itself for dissociation of tissue by pushing the tissue through the mesh of the cell strainer.

DETAILED DESCRIPTION

Figure 1:
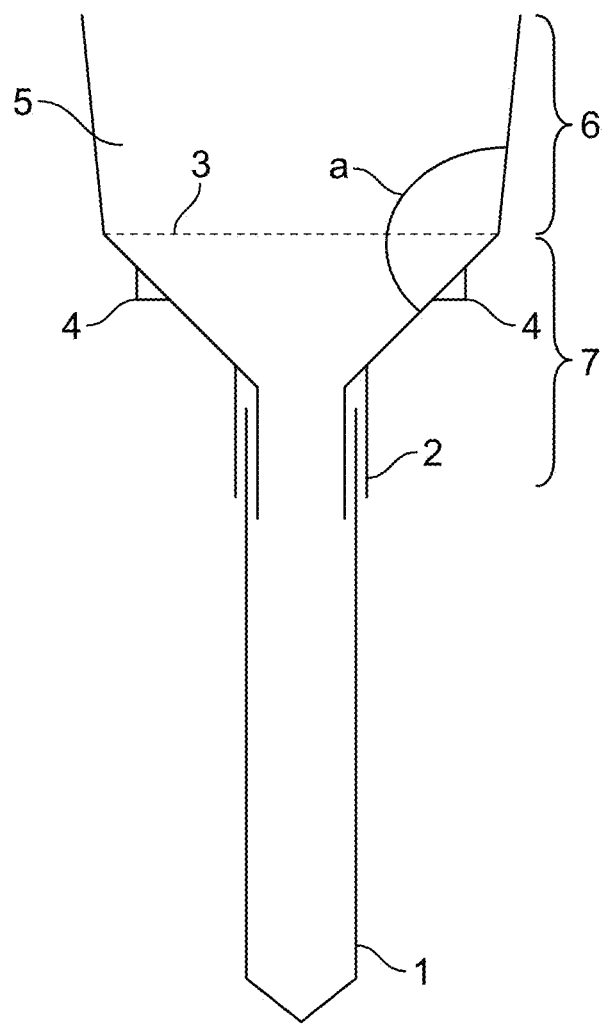
FIG. 1 shows a schematic side view of the present cell strainer.

FIG. 1 shows a schematic side view of a cell strainer according to the invention. A 15 ml standard tube 1 is inserted into the receptacle 2 of the lower portion 7 of the cell strainer. The lower portion 7 has, for resting on the opening of a 50 ml standard tube (not shown), shoulders or flanges 4. The upper portion 6 has the sieve (filter) area 3 and a reservoir volume 5.

The sieve area 3 is not incorporated in a frame but is in the closed body of the upper portion 6. Therefore, the cell strainer can be easily removed from its sterile package without touching the sieve 3, avoiding contamination of the sieve, and according to the invention does not need a grip or handle projecting from any part of the strainer. Tubes with such cell strainers installed can be stored in standard tube racks without difficulty.

In a first embodiment of the invention, the diameter of the filter (sieve) area is larger than the inner diameter of the first and second sections of the lower portion of the cell strainer. Of course, the inner diameter of the first and second sections corresponds to the outer diameter of the tubes to be placed at the receptacle 2 and shoulders or flanges 4. It is possible to utilize filter areas with a smaller diameter than the inner diameter of the first and second section of the lower portion of the cell strainer. In this variant, the upper portion of the cell strainer is provided with more storage volume, but the filter surface area is reduced. For most applications, this variant of the invention is less preferred.

Figure 2:
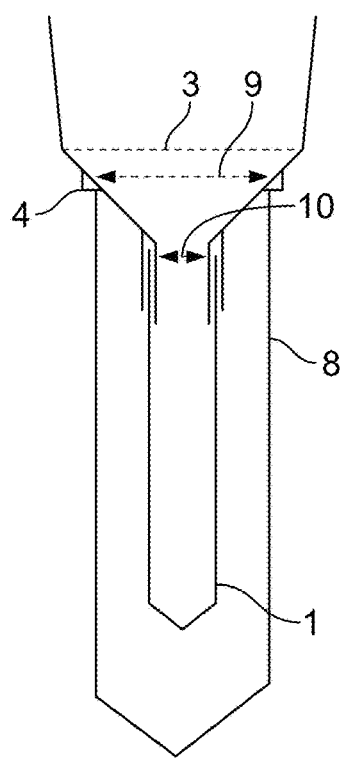
FIG. 2 shows the cell strainer of FIG. 1 with an additional tube.

FIG. 2 shows a side view of a cell strainer with a 15 ml standard tube 1 and a 50 ml standard tube 8 in place. The filter area 3 has a diameter larger than the respective inner diameters 9, 10 of the first and second sections, i.e. at the receptacle 2 and shoulders or flanges 4. Preferably, the diameter of the filter area 3 is at least 1%, preferably 10% to 25% larger than the inner diameter 9 of the first section and at least 25%, preferably 50% to 150% larger than the inner diameter 10 of the second section.

In another embodiment, the upper portion of the cell strainer has an external diameter substantially equal to that of the lid (cover) of a standard 50 ml tube.

Figure 3:
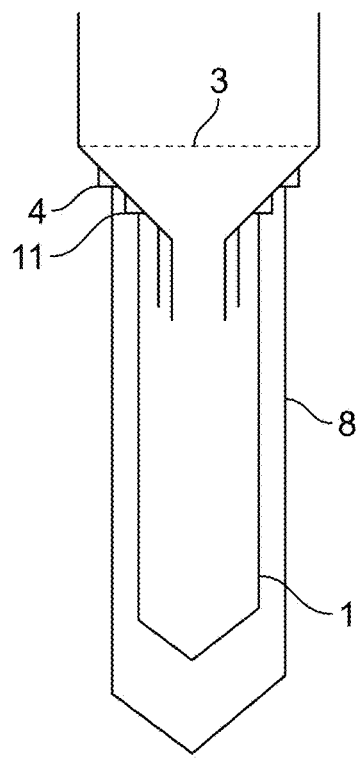
FIG. 3 shows a variant of the FIG. 1 device.

The upper portion of the cell strainer can be substantially cylindrical or cone-shaped. The lower portion is substantially shaped as a cone or can be provided with at least two cone-shaped sections with different external diameters. FIG. 3 shows a cell strainer with a cylindrical upper portion otherwise similar to FIG. 2.

Regardless of their shape, the upper and lower portions of the cell strainer lie at an angle to each other. Especially if using the cell strainer with a 15 ml standard tube, the angle should not be too small to prevent clogging. If the angle is too large, the extensions into the tubes may be too large and the overall size of the cell strainer would prevent stacking of at least two cell strainers. The angle "a" between the upper and lower portions of the cell strainer is preferably in the range of 105° and 165°, as shown in FIG. 1.

In another embodiment of the invention, the cell strainer is provided with an upper portion having an internal diameter and internal space to allow stacking of at least two cell strainers. The upper portion of the cell strainer preferably has volumes of at least 10 ml, especially 15 to 30 ml in FIG. 1.

Stackable cell strainers can be used for sequential or fractionated filtration, i.e. the cell suspension is first filtered through a cell strainer having a large mesh size into a second cell strainer having a smaller mesh size and if necessary into further strainers having an even smaller mesh size. Coarse particles can be removed from a cell suspension without clogging the filter and thus reducing the processing time.

The cell strainer may have two, three, four or five sections in the lower portion with different external diameters with shoulders or flanges to receive openings of tubes with different internal diameters. FIG. 3 shows a cell strainer with two sets of shoulders or flanges 4 and 11 for respective tubes 8 and 12. Particularly, a cell strainer may have two sections of the lower portion with different external diameters fitting into tubes having 15 ml and 50 ml volume. Common tubes having 15 ml and 50 ml volume can be obtained commercially, for example, as BD Falcon™ or Corning CentriStar™ centrifuge tubes.

The shoulders or flanges on the lower portion of the cell strainer are preferably arranged in a way to enable a tilt-free stacking of the cell strainers. The term "shoulders or flanges" used here is intended to encompass any structure such as edges or rims formed on or part of or attached to the lower portion of the cell strainer, which provides suitable mechanical support for a cell strainer on or into the opening of a tube-like vessel. A skilled artesian is aware of such structures which enable the lower portion of the cell strainer to be stacked on a tube in a tilt-free manner.

Figure 5A:
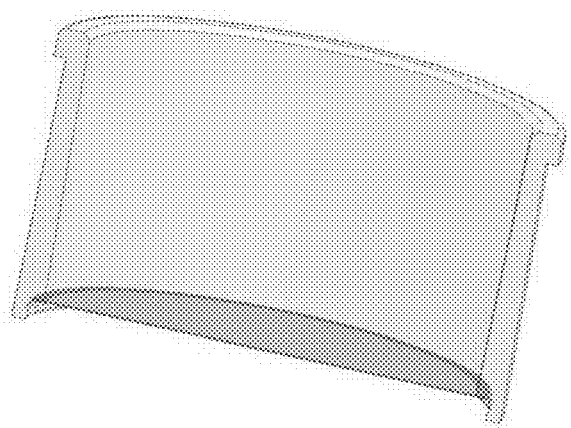
FIGS. 5A, 5B, and 5C show views of a cell strainer with recesses.
Figure 5B:
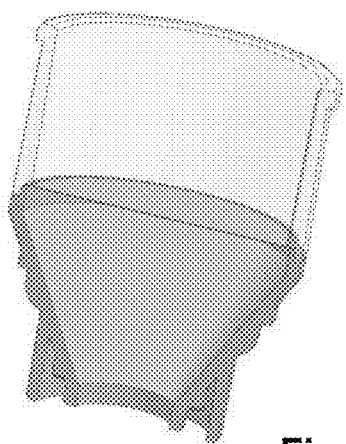
Figure 5C:
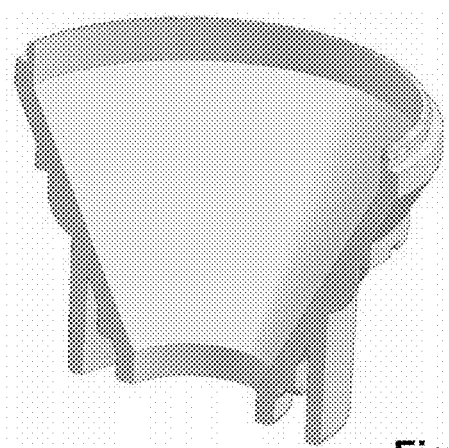

In a further embodiment of the invention, the cell strainer is provided with shoulders or flanges having at least one recess for venting. The shoulders or flanges may include e.g., 1 to 25 recesses for venting. FIGS. 5A, 5B, and 5C show three views of a cell strainer with a plurality of recesses in a shoulder/rim-like support structure on its lower portion. In an embodiment shown in FIG. 6, the cell strainer has rather small flanges with a broad venting area between the flanges. In such case, the cell strainer may have 3 to 10 flanges with venting areas located between the flanges acting the same way as recesses in a shoulder/rim/edge-like structure.

It was found that a filtration area lying in a plane oriented parallel to the direction of flow does not contribute to filter performance or capacity as much as a filtration area oriented in a plane lying perpendicular to the direction of flow. For example, by enlarging the filtration area oriented perpendicular to the direction of flow by 35%, roughly the same filtration throughput is reached as by enlarging the filtration area oriented parallel to the direction of flow by 170%. Accordingly, the present cell strainer is preferably provided with only one filter area oriented perpendicular to the direction of flow of the cell suspension. Therefore, it is more efficient to have a filtration area perpendicular to the flow direction having a diameter bigger than that of the tube than to have the feature of suspending the filter into the tube.

For large amounts of cell suspension to be filtrated, one may provide greater filtration area lying as perpendicular to the direction of flow as possible. For such cases the cell strainer can be provided with an upper portion having at least one filter area lying perpendicular to the direction of flow of the cell suspension and at least one filter area lying in the direction of flow of the cell suspension.

Figure 4:
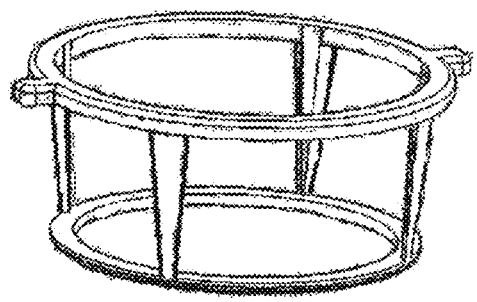
FIG. 4 shows a filter frame for the FIG. 1 device.

At least one filter area of the cell strainer can be provided in a frame located in the upper portion of the cell strainer. The frame can have at least one filtration area lying perpendicular to the direction of flow and/or at least one filter area lying in the direction of flow of the cell suspension. FIG. 4 shows by way of example such a filter frame to be inserted into the cell strainer.

Figures 7A, 7B:
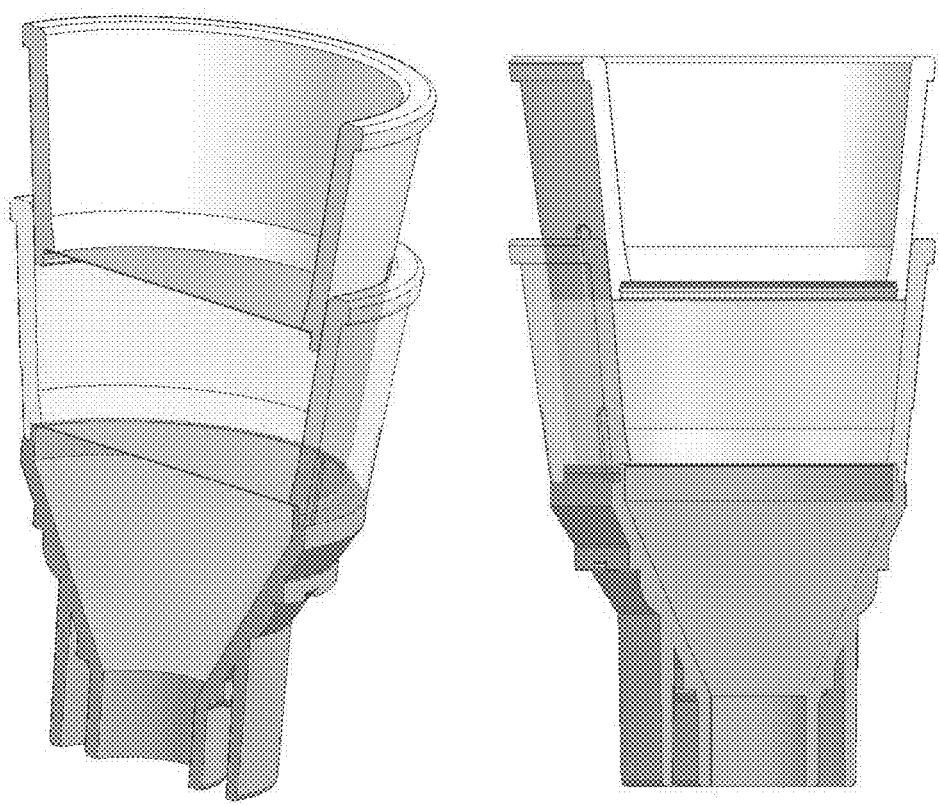
FIGS. 7A, 7B show stacked cell strainers.

The upper and lower portions of the cell strainer according to the invention can be either integrally formed together or formed as separate bodies (see FIGS. 5A, 5B, and 5C). In the first case, the cell strainer is of one piece. If the cell strainer has upper and lower portions which can be separated, the upper portion having the filter area may be disconnected from the lower portion and stacked on a second cell strainer. FIGS. 7A and 7B show two views of stacked cell strainers of this embodiment.

Figure 8:
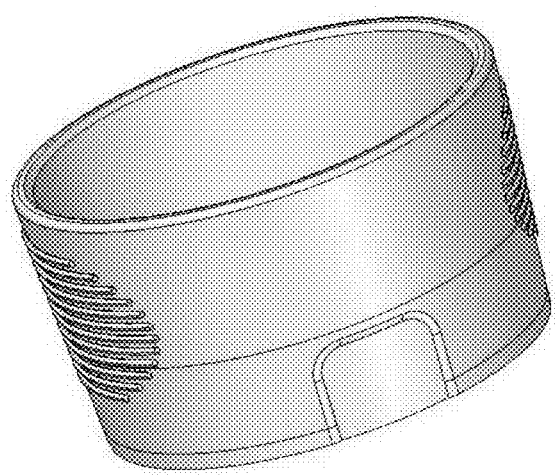
FIG. 8 shows a cell strainer with external grip grooves.

For better handling, especially when the user of the cell strainer is wearing gloves, the upper portion of the cell strainer can be provided with fine ripples or grooves which may be orientated in or perpendicular to the direction of flow. FIG. 8 shows an upper portion of the cell strainer separated from the lower portion and equipped with such grooves.

Figure 6:
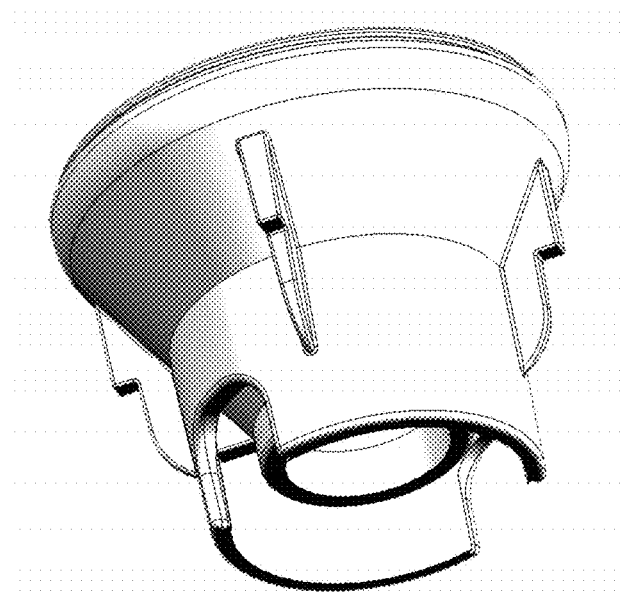
FIG. 6 shows another variant of the cell strainer.

In another embodiment of the invention, the outer walls of the receptacle of the second section of the lower portion are provided with openings. The openings enable the user of the cell strainer to observe the fill level of an installed smaller tube. In addition, it is preferable that the inner walls of the receptacle of the second section of the lower portion are shorter than the outer walls. Both these embodiments are depicted in FIG. 6.

Figure 9:
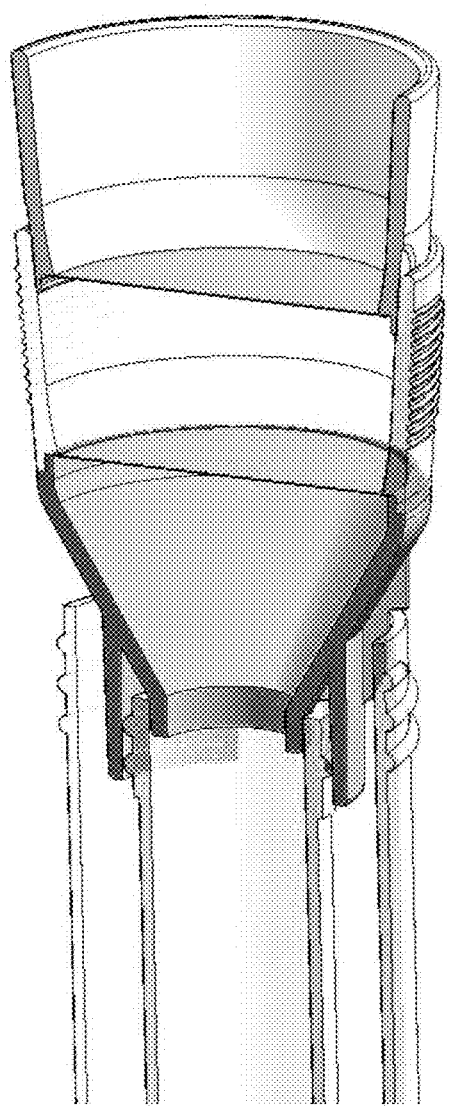
FIG. 9 shows stacked cell strainers.

FIG. 9 shows a side view of stacked cell strainers with a combination of the following features:

The diameter of the filter area is larger than the diameter of the first and second section.

Small flanges with a broad venting area between the flanges.

Upper portion is provided with grooves.

Lower portion is substantially shaped as a cone, at an angle of 105° to 165° with the upper portion.

The receptacle of the second section is shaped to receive the neck of a standard 15 ml tube.

Upper and lower portions of the cell strainer are separate bodies.

The outer walls of the receptacle of the second section of the lower portion are provided with openings to allow controlling the liquid level in the second tube.

The inner walls of the receptacle of the second section of the lower portion are shorter than the outer walls.

FIG. 9 shows for better understanding of the invention two installed tubes, which is not the case in normal use of the cell strainer. It should be noted that not all features of the invention as shown in FIG. 9 need to be implemented simultaneously on a cell strainer.

The cell strainer may be produced from various materials, preferably from plastics such as, for example, polystyrene (PS), polyvinylchloride (PVC), polycarbonate, glass, polyacrylate, polyacrylamide, polymethylmethacrylate (PMMA), polyethylene terephthalate (PET), polytetrafluorethylene (PTFE), thermoplastic polyurethane (TPU), silicone, polyethylene (PE) polypropylene (PP), polyvinyl alcohol (PVA) or compositions including one or more of the above mentioned materials.

The cell strainer according to the invention may have filter areas with mesh sizes between 10 and 500 μm, for example 10, 20, 30, 40, 50, 60, 70, 80, 90, 100, 150, 200 or 500 μm. The filter may be produced from plastics such as polyamide (PA), polystyrene (PS), polyvinylchloride (PVC), polycarbonate, glass, polyethylene terephthalate (PET), polytetrafluorethylene (PTFE), silicone, poly ethylene (PE), poly propylene (PP) and/or polyvinyl alcohol (PVA), and polyethersulfon (PES).

EXAMPLES

The efficiency of a cell strainer according to the invention (as shown in FIGS. 1-3, 5 and 6) and the prior art (EP 0593767, similar to present FIG. 4) were compared. Both cell strainers were fixed in a stand a few mm above a 50 ml Falcon tube so that the filtrate drips into the tube without the risk of a flow stop which sometimes occurs with viscous cell suspensions. A mouse liver cell suspension was created by dissociation of mouse liver in 10 ml PEB with program B on the commercially available (from Miltenyi Biotec) gentleMACS™ Dissociator. The cell suspension was diluted with 90 ml PEB; 9 ml of the diluted cell suspension was put on each cell strainer. The flow-through was collected and the volume was measured.

The cell strainer according to the invention had a bottom filter (surface) area of 346 mm$^2$, whereas the cell strainer according to the prior art (as shown in FIG. 4) had a side filter area of 595 mm$^2$ and a bottom filter area of 346 mm$^2$ (for a total filter area of 941 mm$^2$).

For a better comparison, the side walls of the cell strainer of the prior art were sealed in quarters.

For an efficient cell strainer, it would be expected that the flow-through volume increases proportional to the filter area. As seen in the following table, although the filter area of the cell strainer according to the prior art has 172% of the filter area of the cell strainer according to the invention, its flow-through is greater only by 55%. This is caused by a lower filtration efficiency of the side wall of the filter area, in comparison to that of the bottom filter area.

| Filter | volume of flow-through in mL | Average | Filter area in mm$^2$ | μl/mm$^2$ | % increase of filtrate volume |
|---|---|---|---|---|---|
| prior art (no sealing) | 6.5<br>6.5<br>5.5 | 6.2 | 941 | 6.6 | 55 |
| prior art (one quarter sealed) | 5.3<br>6.1<br>5.7 | 5.7 | 792 | 7.2 | 44 |
| prior art (2 quarters sealed) | 5.1<br>5.3<br>5.5 | 5.3 | 644 | 8.2 | 34 |
| prior art (3 quarters sealed) | 4.5<br>4.7<br>5.1 | 4.8 | 495 | 9.6 | 20 |
| Present | 4.4<br>3.6<br>3.9 | 4.0 | 346 | 11.5 | — |

In another experiment it was shown that an increase of the filter surface area according to the invention by 36% (475 mm$^2$) resulted in higher flow-through volumes than the cell strainer of the prior art (941 mm$^2$).

Given the same filter surface area, the cell strainer according to the invention is more efficient than those of the prior art. For most filtration problems, the filtration capacity of the cell strainer according to the invention is sufficient.

Furthermore, due to its shape, the present cell strainer can be placed securely on both standard 15 ml and 50 ml laboratory tubes, whereas the cell strainer of the prior art fits only into the standard 50 ml laboratory tubes or requires a separate stand.

The invention claimed is:

1. A cell strainer for separating particles from a cell suspension, comprising:
   an upper portion configured to receive a filter lying essentially perpendicular to the direction of flow through the strainer; and
   a lower portion adapted to fit into the openings of at least two tubes with different sized openings;
   wherein the lower portion has a first section defining shoulders or flanges having the diameter of the opening of a first tube and at least one second section having an inner wall and an outer wall configured as a receptacle for the neck of a second tube between the inner wall and the outer wall,
   wherein the inner wall and the outer wall are configured to form a force-fitting hold to the second tube fit between the inner wall and the outer wall,
   wherein the inner wall is shorter than the outer wall,
   wherein the inner wall and the outer wall are parallel to each other and parallel to the direction of flow through the strainer,
   wherein the diameter of the first section is larger than that of the second section,
   wherein the first section is between the upper portion and the second section in a dimension parallel to the direction of flow through the strainer, and
   wherein the lower portion comprises a chamber with a tapered inner surface.

2. The cell strainer according to claim 1, wherein the diameter of the filter is larger than that of the first and second sections.

3. The cell strainer according to claim 1, wherein the shoulders or flanges define at least one recess for venting.

4. The cell strainer according to claim 1, wherein the upper portion is substantially cylindrical shaped and the lower portion is substantially cone shaped, lying one to another at an angle of 105° to 165°.

5. The cell strainer according to the claim 1, wherein the upper portion is substantially cylindrical shaped and the lower portion has at least two cone-shaped sections having different external diameters.

6. The cell strainer according to claim 1, wherein the upper portion comprises at least one filter area lying perpendicular to the direction of flow through the strainer and at least one filter area lying in the direction of flow through the strainer.

7. The cell strainer according to claim 1, wherein the outer diameter of the shoulders or flanges of the first section is substantially equal to the inner diameter of a standard 50 ml tube.

8. The cell strainer according to claim 1, wherein the inner wall and the outer wall of the receptacle of the second section are shaped to receive the neck of a standard 15 ml tube.

9. The cell strainer according to claim 1, wherein the upper portion has a third section having an outer diameter substantially equal to the inner diameter of the upper portion thereby to allow stacking of cell strainers.

10. The cell strainer according to claim 1, wherein the upper and lower portions are integrally formed.

11. The cell strainer according to claim 1, wherein the upper and lower portions are separate bodies.

12. The cell strainer according to claim 1, wherein the outer wall of the receptacle of the second section of the lower portion comprises one or more openings within the outer wall.

* * * * *